United States Patent [19]

Merkle et al.

[11] 4,175,184

[45] Nov. 20, 1979

[54] MANUFACTURE OF 2,1,3-THIADIAZIN-4-ONE-2,2-DIOXIDE DERIVATIVES

[75] Inventors: Hans Merkle; Albrecht Mueller; Karl Zoller, all of Ludwigshafen, Fed. Rep. of Germany

[73] Assignee: BASF Aktiengesellschaft, Ludwigshafen, Fed. Rep. of Germany

[21] Appl. No.: 879,722

[22] Filed: Feb. 21, 1978

[30] Foreign Application Priority Data

Mar. 10, 1977 [DE] Fed. Rep. of Germany ....... 2710382

[51] Int. Cl.$^2$ ........................................... C07D 285/22

[52] U.S. Cl. ..................................... 544/10; 544/11; 260/558 A

[58] Field of Search ..................................... 544/10, 11

[56] References Cited

U.S. PATENT DOCUMENTS 4,014,888 3/1977 McKendry ............................. 544/10

*Primary Examiner*—Ethel G. Love
*Attorney, Agent, or Firm*—Keil & Witherspoon

[57] ABSTRACT

New and valuable process for the manufacture of 2,1,3-thiadiazin-4-one-2,2-dioxide derivatives by reaction of anthranilic acid amide or aminopyridine carboxamide derivatives with sulfur trioxide derivatives to give the sulfamic acid salts, followed by cyclization of these salts.

7 Claims, No Drawings

MANUFACTURE OF 2,1,3-THIADIAZIN-4-ONE-2,2-DIOXIDE DERIVATIVES

The present invention relates to a novel process for the manufacture of 2,1,3-thiadiazin-4-one-2,2-dioxide derivatives by reaction of anthranilic acid amide or aminopyridine carboxamide derivatives with sulfur trioxide derivatives to give the sulfamic acid salts, followed by cyclization of these salts.

German Laid-Open Application DOS No. 2,105,687 discloses the manufacture of 3-alkyl-2,1,3-benzothiadiazin-4-one-2,2-dioxides by reaction of anthranilic acid with alkylamidosulfonyl chlorides in the presence of tertiary amines, followed by cyclization of the sulfamides with phosgene. Further, German Laid-Open Application DOS No. 2,357,063 teaches the manufacture of 2,1,3-benzothiadiazin-4-one-2,2-dioxides by reaction of the appropriate anthranilates with sulfamic acid halides.

We have now found that 2,1,3-thiadiazin-4-one-2,2-dioxide derivatives of the formula

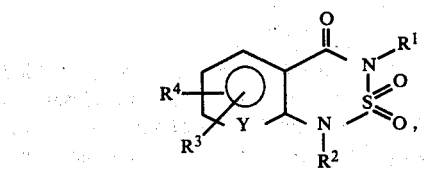

where $R^1$, $R^2$ and $R^3$ are identical or different and each denotes hydrogen, unsubstituted aliphatic, cycloaliphatic or aromatic radicals, or aliphatic, cycloaliphatic or aromatic radicals substituted by halogen, alkyl, alkoxy, haloalkoxy, alkylsulfonyl or dialkylamidosulfonyl, $R^1$ additionally denotes dialkylamino, $R^3$ additionally denotes halogen or trifluoromethyl, $R^4$ denotes hydrogen or alkyl, and Y denotes a $$-\underset{H}{C}-$$

group optionally substituted by $R^3$ or $R^4$ or Y denotes a —N—group, are advantageously obtained if carboxamide derivatives of the formula

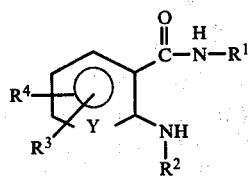

II, where $R^1$, $R^2$, $R^3$, $R^4$ and Y have the above meanings, are reacted with sulfur trioxide or chlorosulfonic acid in the presence of organic bases or with adducts of sulfur trioxide and organic bases, to give the corresponding sulfamic acid salts of the bases of the formula

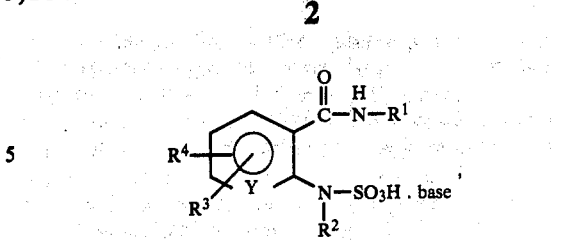

where $R^1$, $R^2$, $R^3$, $R^4$ and Y have the above meanings, and the sulfamic acid salts of the bases or the free sulfamic acid are cyclized with the aid of acid halides or acid anhydrides.

When anthranilic acid-N-isopropylamide is used as the compound of the formula II, picoline as the base, and phosphorus oxychloride as the acid chloride, the reaction may be represented by the following equation:

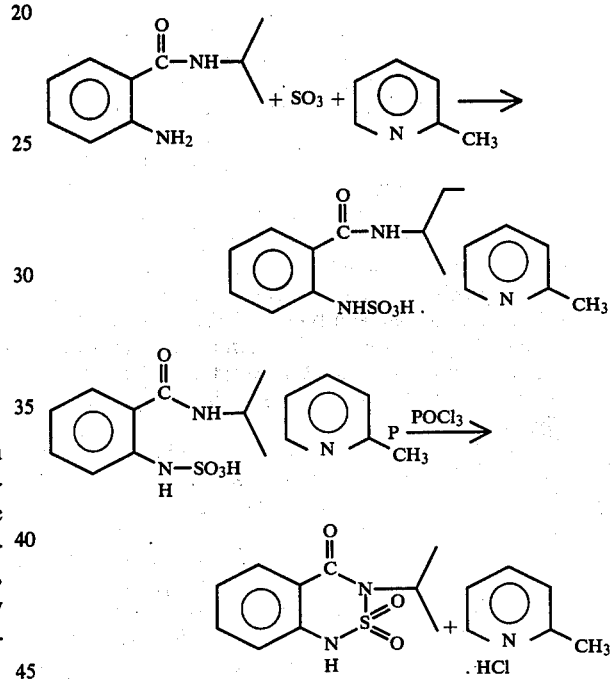

Compared with prior art processes, the process according to the invention, starting from easily accessible and inexpensive materials, surprisingly provides the desired compounds in very high yields and purity, and in a simpler and much more economic manner.

Preferred starting materials II and consequently preferred end products I are those in whose formulae $R^1$ denotes hydrogen, alkyl of 1 to 20, preferably 1 to 10, especially 1 to 4, carbon atoms, cycloalkyl of 3 to 8 carbon atoms, substituted or unsubstituted phenyl, or dialkylamino where alkyl is of 1 to 10 carbon atoms.

$R^2$ denotes for example hydrogen, alkyl of 1 to 20, preferably 1 to 10, carbon atoms, cycloalkyl of 3 to 8 carbon atoms, or substituted or unsubstituted phenyl.

$R^3$ denotes for instance an alkyl substituent of 1 to 10 carbon atoms or halogen. $R^4$ denotes for instance alkyl of 1 to 10 carbon atoms. The alkyl radicals at $R^1$, $R^2$, $R^3$ and $R^4$ may also be substituted by groups inert under the reaction conditions, e.g., alkyl of 1 to 4 carbon atoms, halogen, alkoxy, haloalkoxy, alkylsulfonyl and dialkylamidosulfonyl. The following compounds are for example suitable as starting materials II:

anthranilic acid amide, methyl-, ethyl-, propyl-, isopropyl-, butyl-, isobutyl-, sec-butyl-, tert-butyl-, pentyl-, pentyl-(2)-, pentyl-(3)-, n-hexyl-, n-heptyl-, n-octyl-, n-nonyl-, n-decyl- and 2-ethylhexylamide of anthranilic acid, N',N'-dimethyl-, N',N'-diethyl-, N',N'-methylpropyl-, N',N'-methylisopropyl-, N',N'-dipropyl- and N',N'-diisopropylhydrazide of anthranilic acid, and the abovementioned alkylamides and dialkylhydrazides of N-methyl-, N-ethyl-, N-propyl-, N-isopropyl-, N-butyl-, N-sec-butyl-, N-isobutyl- and N-tert-butylanthranilic acid.

The alkylamides and dialkylhydrazides of 3-methyl-, 4-methyl-, 5-methyl-, 6-methyl-, 3-ethyl-, 4-ethyl-, 5-ethyl-, 6-ethyl-, 3-trifluoromethyl-, 4-trifluoromethyl-, 5-trifluoromethyl-, 6-trifluoromethyl- and 3,5-dimethylanthranilic acid are also excellently suitable as starting compounds. It is also possible to use for instance the alkylamides and dialkylhydrazides of 2-aminopyridine-3-carboxylic acid, and of alkylamino-substituted pyridinecarboxylic acids.

In the process according to the invention, the following organic bases may for instance be used: trialkylamines such as trimethylamine, triethylamine, dimethylethylamine, dimethylpropylamine, dimethylpropylamines, dimethylbutylamines, dimethylcyclohexylamine, and tributylamine; N-methylmorpholine, N-ethylmorpholine, N-methylpiperidine; tertiary amines such as N-ethylimidazole, N-methylpyrrole, pyridine, alkylpyridines, quinoline, lutidene and quinaldine; N,N-dialkylanilines, e.g., dimethylaniline, diethylaniline and methylethylaniline; N-alkyldiphenylamines, e.g., N-methyldiphenylamine and N-ethyldiphenylamine; N,N-dialkylamides, e.g., dimethylformamide and dimethylacetamide; tetraalkyl ureas, e.g., tetramethyl and tetraethyl urea; and Schiff bases, e.g., isopropylideneisopropylamine.

In the sulfonation of aminopyridinecarboxylic acids, these compounds may themselves be the base.

For the cyclization of the sulfamic acid salts of the formula III, for instance organic acid halides, e.g., acetyl chloride, chloroformates, imidoyl chlorides; carboxylic acid anhydrides, e.g., acetic anhydride; inorganic acid halides, e.g., phosgene, phosphorus pentachloride, phosphorus oxychloride, $BF_3$; and inorganic acid anhydrides, e.g., phosphorus pentoxide, are used.

The reaction is expediently carried out by reacting from 0.8 to 1.5, preferably from 0.95 to 1.3, moles of sulfur trioxide with from 0.95 to 2 moles of one of the abovementioned bases, at from $-20°$ to $+100°$ C., preferably from $-10°$ to $+30°$ C., in a diluent or solvent inert under the reaction conditions, e.g., aliphatic, optionally chlorinated hydrocarbons such as methylene chloride, chloroform, carbon tetrachloride, 1,2-dichloroethane and dichloropropane; aromatic, optionally chlorinated hydrocarbons such as benzene, toluene, chlorobenzenes and dichlorobenzene; hydrocarbons such as naphtha, hexane, heptane and octane; ethers such as diethyl ether; amides such as dimethylformamide; or mixtures of such solvents. The base used for the reaction may also serve as the solvent for the reaction. At from $-20°$ to $+100°$ C., preferably from $-10°$ to $+30°$ C., 1 mole of an amide or hydrazide of one of the abovementioned anthranilic acids or aminopyridinecarboxylic acids is added, either as such or as a suspension or solution, e.g., in one of the abovementioned solvents, to the solution or suspension of the sulfur trioxide adduct with the base. After a few minutes the salt of sulfamic acid and the base forms; depending on the reaction conditions, it is either a solution or a suspension. The sulfamic acid may also be prepared by adding the $SO_3$-base adduct as such to a suspension or solution of a compound of the formula II. The mixture is then stirred for from 30 minutes to 2 hours at room temperature before from 1 to 3 equivalents of one of the abovementioned acid chlorides or acid anhydrides are added; the reaction mixtures is then stirred for from 30 minutes to 2 hours at a temperature between room temperature and the boiling temperature of the solvent. The reaction mixture is then hydrolyzed with water and worked up. It is also possible to separate the sulfamic acid salts from the reaction mixture, e.g., by filtration or removal of the solvent, before cyclizing them. The sulfamic acid may also be liberated from the salt, e.g., with hydrogen chloride, and the free acid subsequently cyclized. Generally, however, the reaction will, for economic and operational reasons, be followed by cyclization without separation of the intermediate stage.

The process may be carried out continuously or batchwise and at atmospheric or superatmospheric pressure.

The compounds which may be prepared by the process according to the invention are well-known crop protection agents, especially 3-isopropyl-2,1,3-benzothiadiazin-4-one-2,2-dioxide and its sodium and ammonium salts.

EXAMPLE 1

(a) At 0° C., 17.6 parts (by weight) of $SO_3$ is added over a period of 30 minutes to a solution of 21.5 parts of picoline in 300 parts of 1,2-dichloroethane. After a further 20 minutes, 35.65 parts of anthranilic acid isopropylamide is introduced all at once into the reaction solution. A solution soon forms, from which fine crystals precipitate out after a few minutes. The crystals are isolated by filtration after the solution has been stirred for 1 hour. After drying under a high vacuum, there is obtained 70.2 parts of the colorless picoline salt of 1-(isopropylamidocarbonyl)-phenylsulfamic acid, m.p.: 147° C.

(b) At room temperature, 21 parts of phosphorus oxychloride is added over a period of 5 minutes to a suspension of the picoline salt, and the reaction mixture is slowly heated to reflux temperature; a brown solution forms. After the reaction mixture has been refluxed for 2 hours, it is hydrolyzed with water. The organic phase is washed with water and then extracted 3 times with dilute caustic soda solution. The combined alkaline extracts are acidified with dilute sulfuric acid. The yellowish precipitate which forms is suction filtered and dried. There is obtained 45.6 parts of 3-isopropyl-2,1,3-benzothiadiazin-4-one-2,2-dioxide.

EXAMPLE 2

A suspension of the picoline salt prepared in accordance with Example 1 is introduced over a period of 40 minutes into a solution, heated to reflux temperature, of 30 parts of phosphorus oxychloride in 100 parts of dichloroethane; a pale brown solution forms. After the reaction mixture has been stirred for a further 30 minutes, it is cooled, hydrolyzed at 20° C. with 100 parts of water, and worked up as in Example 1. There is obtained 47 parts of 3-isopropyl-2,1,3-benzothiadiazin-4-one-2,2-dioxide.

EXAMPLE 3

(a) At 0° C., 9.0 parts of $SO_3$ is added over a period of 10 minutes to 11.2 parts of picoline in 100 parts of 1,2-dichloroethane. After the reaction mixture has been stirred for 20 minutes—the reaction temperature being allowed to rise to 15° C.—17.92 parts of anthranilic acid-N',N'-dimethylhydrazide is added all at once, no change in temperature taking place. The colorless suspension which forms is stirred for 1.5 hours at room temperature, and then filtered. After drying at 20° C. in a high vacuum, there is obtained 35.1 parts of the colorless picoline salt of 2-(N',N'-dimethylhydrazidocarbonyl)-phenylsulfamic acid, m.p.: 153° C.

(b) At room temperature, 11 parts of phosphorus oxychloride is added to a suspension of the picoline salt of 2-(N',N'-dimethylhydrazidocarbonyl)-phenylsulfamic acid, and the reaction mixture is slowly heated to reflux. After refluxing for 1 hour, the yellow reaction solution is hydrolyzed with water. The organic phase is washed with water and then extracted several times with dilute caustic soda solution. The combined caustic soda extracts are acidified and the precipitate which forms is suction filtered and dried. There is obtained 22.5 parts of the yellow 3-dimethylamino-2,1,3-benzothiadiazin-4-one-2,2-dioxide, m.p.: 168° C. (from toluene).

EXAMPLE 4

At 0° C., 9 parts of $SO_3$ is added over a period of 15 minutes to a solution of 11 parts of picoline in 100 parts of 1,2-dichloroethane. 19.2 parts of 8-methylanthranilic acid isopropylamide is then added to the reaction solution, and the suspension which forms is stirred for 1 hour at room temperature. 15.4 parts of phosphorous oxychloride is then added and the reaction mixture is refluxed for 2 hours. Conventional working up gives 24 parts of 8-methyl-3-isopropyl-2,1,3-benzothiadiazin-4-one-2,2-dioxide (m.p.: 124° C.).

EXAMPLE 5

At 20° C., 9 parts of $SO_3$ is added over a period of 15 minutes to a solution of 12 parts of triethylamine in 100 parts of 1,2-dichloroethane. After a further 30 minutes, 17.8 parts of anthranilic acid isopropylamide is added to the yellow reaction solution. The suspension which forms is stirred for 1 hour at room temperature, 12 parts of phosphorus oxychloride is then added, and the mixture is refluxed for 2 hours. Conventional working up gives 22 parts of 3-isopropyl-2,1,3-benzothiadiazin-4-one-2,2-dioxide.

EXAMPLE 6

At 10° C., 8.5 parts of $SO_3$ is added over a period of 15 minutes to a solution of 14 parts of N',N'-dimethylcyclohexylamine in 100 parts of 1,2-dichloroethane. After a further 20 minutes, 17.8 parts of anthranilic acid isopropylamide is added. The initially voluminous suspension gradually turns into a brown solution. After 90 minutes' stirring, 15 parts of phosphorous oxychloride is added and the mixture refluxed for 2 hours. There is obtained 23 parts of 3-isopropyl-2,1,3-benzothiadiazin-4-one-2,2-dioxide.

EXAMPLE 7

At 0° C., 9 parts of $SO_3$ is dripped over a period of 15 minutes into a solution of 15 parts of dimethylaniline in 100 parts of dichloroethane. 17.8 parts of anthranilic acid isopropylamide is added to the greenish-yellow reaction solution. The brown reaction solution is stirred for 2 hours at room temperature, 15 parts of phosphorus oxychloride is added, and the mixture refluxed for 2 hours. The mixture is then cooled to 20° C. before being subjected to conventional working up. There is obtained 22.8 parts of 3-isopropyl-2,1,3-benzothiadiazin-4-one-2,2-dioxide.

EXAMPLE 8

At 0° C., 9 parts of $SO_3$ is added over a period of 10 minutes to a solution of 14.9 parts of quinoline in 150 parts of dichloroethane. After 90 minutes, 17.8 parts of anthranilic acid isopropylamide is added at room temperature to the colorless suspension, and the mixture is stirred for 2 hours. 12 parts of phosphorus oxychloride is then added. After a few minutes at room temperature, 3-isopropyl-2,1,3-benzothiadiazin-4-one-2,2-dioxide is detectable by thin-layer chromatography. The mixture is stirred for a further 2 hours at 55° C. and overnight at room temperature. After working up in the conventional manner, there is obtained 23.2 parts of 3-isopropyl-2,1,3-benzothiadiazin-4-one-2,2-dioxide.

EXAMPLE 9

At 0° C., 9 parts of $SO_3$ is dripped over a period of 15 minutes into 18 parts of tetramethylurea in 100 parts of dichloroethane. 17.8 parts of anthranilic acid isopropylamide is added to the colorless reaction solution containing a few crystals. After some time, a brown solution forms to which, after 1 hour, 15 parts of phosphorus oxychloride is added at room temperature. A thin-layer chromatograph of the reaction solution after 30 minutes at room temperature already reveals fairly large amounts of 3-isopropyl-2,1,3-benzothiadiazin-4-one-2,2-dioxide. Cyclization is completed by refluxing the mixture for 1 hour, after which it is worked up conventionally. There is obtained 20.5 parts of 3-isopropyl-2,1,3-benzothiadiazin-4-one-2,2-dioxide.

EXAMPLE 10

20 parts of phosphorus pentachloride is added to 0.2 mole of a picoline salt suspension (according to Example 1) and the orange-colored suspension is initially stirred at room temperature (3-isopropyl-2,1,3-benzothiadiazin-4-one-2,2-dioxide is detectable by thin-layer chromatography after only a short time). The reaction mixture is then refluxed for 40 minutes, whereupon an orange solution forms. After conventional working up, 43.0 parts of 3-isopropyl-2,1,3-benzothiadiazin-4-one-2,2-dioxide is obtained.

EXAMPLE 11

28 parts of phosphorus pentoxide is added to 0.2 mole of a picoline salt suspension (according to Example 1); the suspension agglomerates to a certain extent. Refluxing is effected for 2 hours, the mixture not completely dissolving. Conventional working up gives 35 parts of 3-isopropyl-2,1,3-benzothiadiazin-4-one-2,2-dioxide.

EXAMPLE 12

A sulfamic acid salt suspension is prepared as described in Example 1. 0.5 part of dimethylformamide is then added, and phosgene is gassed in for 2 hours at room temperature. A dark brown solution forms, which is hydrolyzed with 100 parts of water. Conventional working up gives 20 parts of 3-isopropyl-2,1,3-benzothiadiazin-4-one-2,2-dioxide.

EXAMPLE 13

10 parts of acetic anhydride is added to the sulfamic acid salt suspension mentioned in Example 12, and the mixture refluxed for 2 hours. Conventional working up gives 15 parts of 3-isopropyl-2,1,3-benzothiadiazin-4-one-2,2-dioxide.

EXAMPLE 14

5 parts of acetyl chloride is added to the sulfamic acid salt suspension mentioned in Example 12, and the mixture refluxed for 2 hours. Conventional working up gives 10 parts of 3-isopropyl-2,1,3-benzothiadiazin-4-one-2,2-dioxide.

EXAMPLE 15

At 0° C., 9 parts of SO₃ is added over a period of 10 minutes to a solution of 15 parts of picoline in 150 parts of 1,2-dichloroethane. After the mixture has been stirred for 20 minutes, 17.9 g of 2-aminopyridine-3-carboxylic acid isopropylamide is added all at once. The colorless solution which forms is stirred for 2 hours at room temperature. 15.4 parts of phosphorus oxychloride is then added. Upon refluxing for 2 hours, the reaction mixture turns into a brown solution. It is hydrolyzed with water, and the organic phase is washed and dried over sodium sulfate. The filtered organic phase is then evaporated to dryness. There is obtained 21.5 parts of 3-isopropyl-1H-pyridino-[3,2-e]-2,1,3-thiadiazin-4-one-2,2-dioxide; m.p.: 190° C.

We claim:

1. A process for the production of a compound of the formula

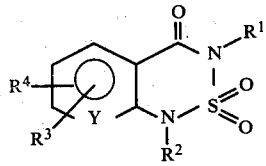

where $R^1$, $R^2$ and $R^3$ are identical or different and each is hydrogen, unsubstituted aliphatic, cycloaliphatic or aromatic hydrocarbon radicals, or aliphatic, cycloaliphatic or aromatic hydrocarbon radicals substituted by halogen, alkyl, alkoxy, haloalkoxy, alkylsulfonyl or dialkylamidosulfonyl, $R^1$ additionally may be dialkylamino, $R^3$ additionally may be halogen or trifluoromethyl, $R^4$ is hydrogen or alkyl, and Y is a

group optionally substituted by $R^3$ or $R^4$ or Y is a —N— group, which process comprises reacting a carboxamide compound of the formula

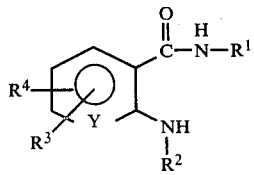

where $R^1$, $R^2$, $R^3$, $R^4$ and Y have the above meanings, with sulfur trioxide or chlorosulfonic acid in the presence of an organic base, or with adducts of sulfur trioxide and organic bases, to give the corresponding sulfamic acid salt of the formula

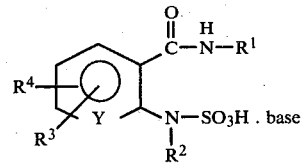

where $R^1$, $R^2$, $R^3$, $R^4$ and Y have the above meanings, and then cyclizing said sulfamic acid salt with the aid of a compound selected from the group consisting of acid halides and acid anhydrides.

2. The process of claim 1 where $R^1$ is hydrogen, alkyl of 1 to 20 carbon atoms, cycloalkyl of 3 to 8 carbon atoms, substituted or unsubstituted phenyl, or dialkylamino where each alkyl thereof contains 1 to 10 carbon atoms; $R^2$ is hydrogen, alkyl of 1 to 20 carbon atoms, cycloalkyl of 3 to 8 carbon atoms, or substituted or unsubstituted phenyl; $R^3$ is alkyl of 1 to 10 carbon atoms or halogen; and $R^4$ is alkyl of 1 to 10 carbon atoms.

3. The process of claim 2 where said alkyl of said $R^1$ and $R^2$ contains 1 to 10 carbon atoms.

4. A process for producing 3-isopropyl-2,1,3-benzothiadiazin-4-one-2,2-dioxide according to claim 1.

5. A process for producing 8-methyl-3-isopropyl-2,1,3-benzothiadiazin-4-one-2,2-dioxide according to claim 1.

6. A process for producing 3-isopropyl-1H-pyridino-[3,2-e]-2,1,3-thiadiazin-4-one-2,2-dioxide according to claim 1.

7. A process for the production of a compound of the formula

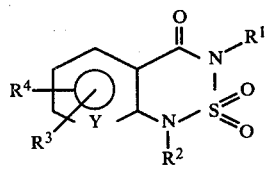

where $R^1$, $R^2$ and $R^3$ are identical or different and each is hydrogen, unsubstituted aliphatic, cycloaliphatic or aromatic hydrocarbon radicals, or aliphatic, cycloaliphatic or aromatic hydrocarbon radicals substituted by halogen, alkyl, alkoxy, haloalkoxy, alkylsulfonyl or dialkylamidosulfonyl, $R^1$ additionally may be dialkylamino, $R^3$ additionally may be halogen or trifluoromethyl, $R^4$ is hydrogen or alkyl, and Y is a

group optionally substituted by $R^3$ or $R^4$ or Y is a —N— group, which process comprises reacting a carboxamide compound of the formula

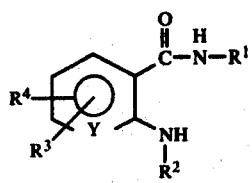

where $R^1$, $R^2$, $R^3$, $R^4$ and Y have the above meanings, with sulfur trioxide or chlorosulfonic acid in the presence of an organic base, or with adducts of sulfur trioxide and organic bases, to give the corresponding sulfamic acid salt of the formula

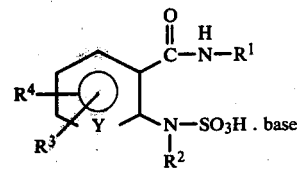

where $R^1$, $R^2$, $R^3$, $R^4$ and Y have the above meanings, converting said acid salt to the corresponding sulfamic acid, and then cyclizing said acid.

* * * * *